July 8, 1947. T. A. ADREY Plant Pat. 742
TABERNAEMONTANA PLANT
Filed Sept. 6, 1946
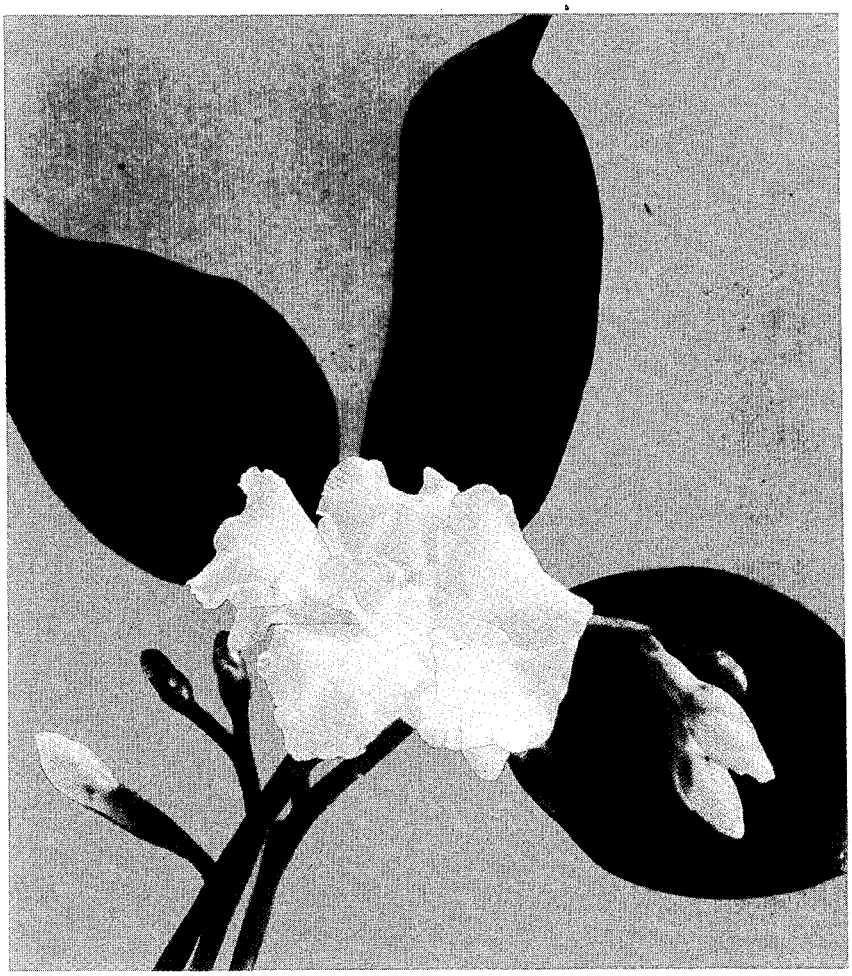
Inventor
T. A. Adrey.
By Robb & Robb
His Attorneys Patented July 8, 1947

Plant Pat. 742

UNITED STATES PATENT OFFICE

742

TABERNAEMONTANA PLANT

Toufic A. Adrey, Bulls Head, Staten Island, N. Y.

Application September 6, 1946, Serial No. 695,166

1 Claim. (Cl. 47—60)

The present discovery relates to a new and distinct variety of Tabernaemontana, originating as a sport of *Tabernaemontana coronaria,* well known as a typical member of the Dogbane family. Because of the similarity of the flowers in appearance to a gardenia, it is frequently classified by the public as such though improperly so since the true gardenia is a member of the Madder family. The distinction between the present plant and the gardenia is easily determined when the two are cut, since this new variety exudes a gummy substance and that is not characteristic of a gardenia.

To best understand the origination of this new variety, it is desirable to refer somewhat fully to the parent plant type to more clearly bring out the points of novelty and distinctions applying to the new variety, particularly in view of the claim that the development of the latter has resulted in a definite plant type not heretofore existing.

The parent plant type is a tender shrub which ordinarily bears what may be termed double flowers, definitely consisting of only two circles of five petals each, or ten petals in all. These flowers might readily pass for single flowers for the reason that the spreading petals of the upper row are somewhat longer than those of the lower circle and are so broad as to overlap each other and thus hide the lower petals.

For the purpose of comparison, in the parent type, the cylindrical tube of the salver-form flower is about seven-eighths of an inch in length, and the widely spreading limb measures from about one to two inches across. The five lower petals of the limb are usually narrowly obovate and a little shorter than the upper ones, and their slightly upturned edges are ruffled. The five upper petals are roundish except for the broadly truncate apex which is responsible for the triangular appearance. These petals are conspicuous for their width, often one and one-quarter inches wide. Expanded, they are rather flat except for some drooping wave about the middle of the truncate apex. Their margins are narrowly frilled and sometimes slightly wavy.

Plants of the parent type occasionally sported, it was observed, and produced a very small percentage of flowers of more than 10 petals—sometimes 13 to 15 petals, borne on more vigorous branches, which because of their larger size, improved doubling, and perfection of flower pattern, obviously were superior to the 10-petaled kind. Observing this fact, and the different behavior of the sporting plants, I established a definite program of rigorous selection from generation to generation, running over a period of many years with the objective of developing better and still better plants with steadily increasing quantitative yield of flowers with petals in excess of the 10-petal type of the original plant, until I finally obtained the present variety, or improved plant type, wherein all the flowers produced thereby have an excess of petals over the 10-petal production of the original parent plant.

In accomplishing the objective, I noted that this new variety presented three important or dominating structural features of distinction from all previous *Tabernaemontana coronaria,* all pertaining to flower pattern. First, there are fifteen to eighteen petals to each flower; secondly, only ten petals thereof participate in the formation of the salverform ground-pattern consisting of a cylindrical tube and a spreading limb; and thirdly, the 5 to 8 excess petals partake in the formation of an accessory, central adjunct which otherwise leaves the salverform ground-pattern entirely intact and undisturbed as in the basic 10-petaled parental flower pattern.

Referring to other distinctions in this new variety, the flower tube is stouter and longer, being one inch or more in length, and as to the limb, the ornamental details far excel those of the original parent variety. That is to say, the lower petals are better developed. The upper petals are narrower, nearly obovate and obtuse or acute at the apex instead of broadly truncate. Their sides and outer end are distinctly and conspicuously wavy in elegant curves and, in addition, are gracefully bordered by a frilled and crimped margin whose edge is erose and erose-laciniate. The combined effect of said characteristics in regard to the upper petals is such that it allows the lower petals to readily show up in top-view, as well as in side-view.

The prominently distinguishing feature of the new variety flower is the central crown, made up by the five to eight petals which do not participate in the formation of the spreading limb. Developing from a cup-like base, the grotesque, progressively changing appearance of the crown results from the cramped, crimped, plaited, and frilled condition of the entangled mass of petals, due to the latter's failure to extricate their inwardly pointing margin. At the early exposure a mere knob, it takes on the form of an at first conveniently pointed, later open, crown from which it develops into an enlarged tangle of petals, always retaining the characteristic crimped condition, as also a certain independence of appearance all of its own.

Aside from the superior merit in size, form, and ornamental details, the delicately sweet-scented flower of the new variety possesses the alditional distinction of superior lasting quality. Without fading and wilting, the flowers last fully twice as long as the old-type 10-petaled flowers. Even as cut flowers, they last five days or longer. On the other hand, the number of flowers in each individual bunch is smaller, actually numbering one to six for each openly cymose cluster against one to ten in case of the 10-petaled ones of the parent plant type. The clusters are carried on three to five inches long, stoutish and stiff peduncles, which arise from the fork of branches.

The new variety, furthermore, is a stronger and more vigorous plant type than the original parent type. Its evergreen leaves are from three to five inches long, oblong in shape, or else, ovate-oblong or obovate-oblong, abruptly and acuminatedly pointed, short-petioled, firm in texture, distinctly and saturatedly vivid in color, slightly glossy, and are well borne in an ascendingly spreading position. What would otherwise be a flat surface monotony, is here pleasantly vivified by the rhythmically alternating waves which ascend in V-shaped fashion toward the margin of the leaf, while in the insunken intervals the gracefully curved veins accompany the waves in a practically paralleled direction.

In the drawings the illustration shows a specimen of this new variety including buds, flower and foliage.

By way of summary of the above and enlargement as to other novel features, the following is a detailed description of this new variety, color terminology being in accord with the usual dictionary meaning:

Type: Tender; tall; greenhouse; sport; for cut flowers.
Discovery: At Florence, Alabama.
Propagation: Holds its distinguishing characteristics through succeeding propagations by cuttings.

*Flower*

Locality where grown: Florence, Alabama.
Flowers borne: Singly, two to six blooms and buds on peduncle stem three to five inches long.
Quantity of bloom: Abundant in greenhouse.
Continuity: Continuous.
Fragrance: Moderate; penetrating.
Bud:
- *Peduncle.*—Short; slender; stiff; green.
- *Before calyx breaks.*—Size—small. Form—long; pointed.
- *As calyx breaks.*—Color—greenish white.
- *As first petal opens.*—Size—small. Form—flat. Color—outside and inside, satin white.
- *Opening.*—Opens up well.

Bloom:
- *Size.*—When fully open—large; 2½ to 3 inches.
- *Petalage.*—Double (3 rows, many petals, usually with no stamens showing); arranged regularly.
- *Form.*—Cupped, full, high center.

Petals: Leathery; soft; with inside satiny.
- *Shape.*—Outside—round; obovate; crimped; ruffled; pleated. Intermediate—obovate.

This description of a newly opened flower was made from a plant grown in a greenhouse in the month of July 1945, at Florence, Alabama:

- *Color.*—Outside petal: outside surface—white; inside surface—white. Intermediate petal: outside surface—white; inside surface—white. Inner petal: outside surface—white; inside surface—white.

This description was made from a plant that was open for three days in a greenhouse in the month of August 1945, at Florence, Alabama:

- *Color.*—Outside petal: outside surface—white; inside surface—white. Inside petal: outside surface—white; inside surface—white.
- *General color effect.*—Newly opened flower—white. Three days open—white.
- *Behavior.*—Only age turns it yellow.
- *Flower longevity.*—On bush in greenhouse—5 days. Cut flowers grown in greenhouse kept at living temperatures 5 to 7 days.

*Reproductive organs*

Stamens: Tucked in calyx.
Pollen: Very sparse.
Pistils: Very few.
Styles: Very even.
Stigma: Light yellow.
Ovaries: All enclosed in calyx.
Sepals: Permanent; short; recurved.
- *Color.*—Inside—white. Outside—white.

Seeds: Few; small.

*Plant*

Foliage:
- *Leaves.*—Normally abundant; large; heavy; leathery; glossy; wrinkled.
- *Leaflets.*—Shape—oval; ovoid. Margin—doubly serrate.
- *Color.*—Mature—upper surface—dark green; under surface—very dark green. Young—upper surface—very light green; under surface—light green.
- *Disease resistance.*—Good.

Growth:
- *Habit.*—Upright; branched out.
- *Growth.*—Vigorous.
- *Canes.*—Heavy.
- *Main Stems.*—Color—tan to light brown.
- *Branches.*—Color—green.
- *New shoots.*—Color—green.

I claim:

A new and distinct variety of Tabernaemontana plant characterized dominantly as to novelty by its production of flowers having fifteen to eighteen petals, ten of which participate in the formation of the salverform ground pattern and the remainder of which form a central adjunct or crown independent of the ground pattern aforesaid, the flower tube being stouter and longer than that of its parent variety; by the distinctive shape and form of the flower petals; by the delicately sweet-scented fragrance of the flowers and their long lasting, non-fading quality; by its strong and vigorous habit of growth; and by the shape and arrangement of its foliage, substantially as shown and described.

TOUFIC A. ADREY.